United States Patent [19]

Tokunaga et al.

[11] Patent Number: 4,985,432

[45] Date of Patent: * Jan. 15, 1991

[54] 5H-1,3,4-THIADIAZOLO(3,2-A)PYRIMIDIN-5-ONE DERIVATIVES AND AGRICULTURAL-HORTICULTURAL FUNGICIDE COMPOSITION CONTAINING THE SAME

[75] Inventors: Yukio Tokunaga; Koichiro Kaku, both of Shizuoka; Yoshiyuki Kojima, Kakegawa; Shinichiro Maeno; Nobumitsu Sawai, both of Shizuoka; Yasuo Saso, Miyagi, all of Japan

[73] Assignees: Kumiai Chemical Industry Co., Ltd.; Ihara Chemical Industry Co., Ltd., both of Tokyo, Japan

[*] Notice: The portion of the term of this patent subsequent to May 3, 2005 has been disclaimed.

[21] Appl. No.: 406,184

[22] Filed: Sep. 13, 1989

Related U.S. Application Data

[63] Continuation of Ser. No. 34,922, Apr. 6, 1987, abandoned.

[30] Foreign Application Priority Data

Apr. 7, 1986 [JP] Japan .................................. 61-78099

[51] Int. Cl.$^5$ ........................................... A01N 43/54
[52] U.S. Cl. ..................................... 514/258; 544/235
[58] Field of Search ........................ 544/255; 514/258

[56] References Cited

U.S. PATENT DOCUMENTS

| | | | |
|---|---|---|---|
| 4,742,063 | 5/1988 | Tokunaga et al. | 514/258 |
| 4,866,064 | 9/1989 | Tokunaga et al. | 514/258 |
| 4,872,901 | 10/1989 | Aoki | 544/255 |

FOREIGN PATENT DOCUMENTS 52-118494 10/1977 Japan .................................. 544/255

OTHER PUBLICATIONS

Okabe et al., Jour. Fac. Agr., Kyushu Univ., vol. 19, pp. 91–102 (1975).
Suiko et al., (I), Agric. Biol. Chem, vol. 41 (No. 10), pp. 2047–2053 (1977).
Suiko et al., (II), Agric. Biol. Chem., vol. 43 (No. 4), pp. 747–752 (1979).
Chemical Abstracts, vol. 87, No. 3, Jul. 18th, 1977, p. 153.
Abstract No. 17148y, Columbus, Ohio, U.S.A., Maekawa Kuzuyuki et al., "Control of Seedling Growth by Pseudopurine . . . ".

Primary Examiner—Donald G. Daus
Attorney, Agent, or Firm—Oblon, Spivak, McClelland, Maier & Neustadt

[57] ABSTRACT

A new class of 5H-1,3,4-thiadiazolo[3,2-a]pyrimidin-5-one derivatives were synthesized. They are useful as agricultural-horticultural fungicides.

6 Claims, No Drawings

5H-1,3,4-THIADIAZOLO(3,2-A)PYRIMIDIN-5-ONE DERIVATIVES AND AGRICULTURAL-HORTICULTURAL FUNGICIDE COMPOSITION CONTAINING THE SAME

This application is a continuation of application Ser. No. 034,922, filed on Apr. 6, 1987, now abandoned.

FIELD OF THE INVENTION

This invention relates to a class of novel 5H-1,3,4-thiadiazolo[3,2-a]pyrimidin-5-one derivative and a novel agricultural-horticultural fungicidal composition containing said derivative.

BACKGROUND OF THE INVENTION

Hithertofore, it is known that 5H-1,3,4-thiadiazolo[3,2-a]pyrimidin-5-one derivatives have physiological activities and applications thereof as various medicinals have been studied.

For instance, the 5H-1,3,4-thiadiazolo[3,2-a]pyrimidin-5-one derivatives represented by the general formula

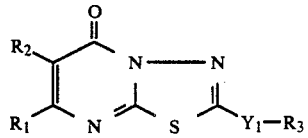

wherein $R_1$ stands for an alkyl group or an aryl group; $R_2$ stands for a hydrogen atom, a halogen atom, a nitro group, a carbakoxy group or an alkyl group; $R_3$ stands for an alkyl group or an aralkyl group; $Y_1$ stands for —SO— or —$SO_2$—, is known to be effective for controlling propagation of cancer cells (Japanese Laying-Open Patent Publication No. 52-118494 (1977)).

The 5H-1,3,4-thiadiazolo[3,2-a]pyrimidin-5-one derivatives represented by the general formula

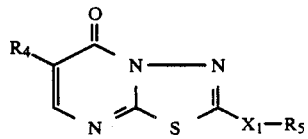

wherein $R_4$ stands for a 1H-tetrazol-5-yl group, a 2H-tetrazol-5-yl group, a carboxyl group or an alkoxycarbonyl group; $R_5$ stands for an aryl or heteroaryl group unsubstituted or substituted with an alkyl group, an alkoxy group, a hydroxy group or halogen; $X_1$ stands for an alkylene group, an alkenylene group, or an alkynylene group, which may have an oxygen atom or a sulfur atom or —$SO_2$— at its end and may be substituted with one or more straight chain alkyl groups, cyclic alkyl groups or $R_5$, and their physiologically acceptable salts are known to have excellent anti-allergic activity (Japanese Laying-Open Patent Publication No. 58-177997 ('83)).

As described above, several kinds of 5H-1,3,4-thiadiazolo[3,2-a]pyrimidin-5-one derivatives are known by now. However, their biological activities relate to medicines, and nothing is known about their biological activities as agricultural chemicals.

The object of the invention is to provide a novel 5H-1,3,4-thiadiazolo[3,2-a]pyrimidin-5-one derivatives which has excellent biological activities as an agricultural chemical and a useful agricultural-horticultural fungicide preparation containing said derivative.

We paid attention to the thiadiazolopyrimidin-5-one skeleton, which is known to be useful as medicinal, and synthesized many novel derivatives thereof. As a result, we found that a specific class of 5H-1,3,4-thiadiazolo[3,2-a]pyrimidin-5-one derivatives exhibit very excellent biological activities as agricultural fungicides. On the basis of this finding, we have completed this invention.

DISCLOSURE OF THE INVENTION

That is, the present invention provides a 5H-1,3,4-thiadiazolo[3,2-a]pyrimidin-5-one derivative represented by the general formula (I)

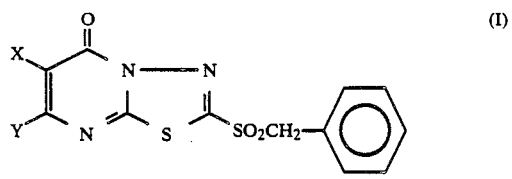

wherein X is a hydrogen atom, a halogen atom, an alkyl group, an alkoxy group, a phenyl group, a phenoxy group, a cyano group or a nitro group; and Y is a hydrogen atom, a halogen atom, a haloalkyl group, an alkoxy group, an alkynyl group which may be substituted with a phenyl group or a cyano group, and an agricultural-horticultural fungicidal composition containing said derivative.

More preferred compounds are those of the general formula (I) wherein X is a hydrogen atom, a halogen atom, a lower alkyl group, a lower alkoxy group or a phenyl group; and Y is a hydrogen atom, a halogen group, a chloroalkyl group or a $C_{2-3}$-alkynyl group which may be substituted with a phenyl group, a cyano group.

Still more preferred compounds are those of the general formula (I) wherein X is a hydrogen atom, a halogen atom, a methyl group, an ethyl group, a methoxy group, an ethoxy group or a phenyl group; Y is a hydrogen atom, a halogen atom, or a cyano group.

Still more preferred compounds are those of the general formula (I) wherein X is a hydrogen atom and Y is a hydrogen atom, a halogen atom or a cyano group, and those of the general formula (I) wherein X is a halogen atom, a methyl group, an ethyl group, a methoxy group, an ethoxy group, or a phenyl group, and Y is a hydrogen atom.

Most preferred compounds are:
2-benzylsulfonyl-7-fluoro-5H-1,3,4-thiadiazolo[3,2-a]pyrimidin-5-one,
2-benzylsulfonyl-6-methyl-5H-1,3,4-thiadiazolo[3,2-a]pyrimidin-5-one,
2-benzylsulfonyl-6-methoxy-5H-1,3,4-thiadiazolo[3,2-a]pyrimidin-5-one,
2-benzylsulfonyl-6-fluoro-5H-1,3,4-thiadiazolo[3,2-a]pyrimidin-5-one,
2-benzylsulfonyl-6-chloro-5H-1,3,4-thiadiazolo[3,2-a]pyrimidin-5-one,
2-benzylsulfonyl-7-cyano-5H-1,3,4-thiadiazolo[3,2-a]pyrimidin-5-one, and
2-benzylsulfonyl-5H-1,3,4-thiadiazolo[3,2-a]pyrimidin-5-one.

The 5H-1,3,4-thiadiazolo[3,2-a]pyrimidin-5-one derivatives of the present invention are novel compounds and specific examples thereof are given in Table 1. The compound number indicated therein is referred to to represent the compound hereinafter.

TABLE 1

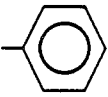

The compounds of the present invention can be prepared by oxidizing a compound represented by the general formula (II)

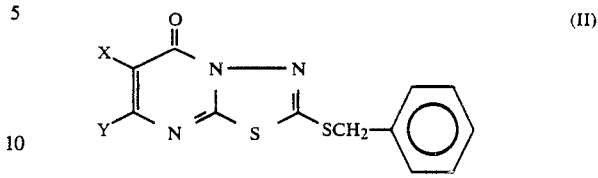

wherein X and Y are as defined with respect to formula (I).

The oxidation of the compound of the general formula (II) can be performed by any method employed for oxidation of organic sulfide compounds.

Examples of the employable oxidizing agent are hydrogen peracids, organic peracids such as m-chloroperbenzoic acid, "OXONE" (trade name, a reagent containing potassium hydrogen peroxosulfate marketed by Du Pont Company), etc.

In addition to the oxidation reagent, an acid catalyst such as acetic acid, a metallic catalyst such as sodium tungstate, for instance, can be used in order to promote the oxidation reaction.

Examples of the solvent used for the oxidation reaction are water; halogenated hydrocarbons such as dichloromethane, chloroform, carbon tetrachloride, chlorobenzene, etc.; fatty acids such as acetic acid, propionic acid, etc.; ketones such as acetone, methylethyl ketone, etc.; amides such as dimethylformamide, dimethylacetamide, etc.; alcohols such as methyl alcohol, ethyl alcohol, etc.; hydrocarbons such as hexane, petroleum ether, benzene, etc.

Oxidation is carried out in a temperature range of $-20°$ C. to the boiling point of the used solvent.

The amount of the used oxidizing agent is usually twice the equivalent quantity of the used compound of the general formula (II) or more, but there is no strict limitation therefor.

The compounds of the general formula (II) are novel substances and can be prepared from 2-amino-5-benzylthio-1,3,4-thiadiazole (III) by the three methods (A, B or C) described below in which 2-amino-5-benzylthio-1,3,4-thiadiazole (III) is reacted with a β-ketoester derivative (IV), a β-formylester or 2-propenate derivative (VI) or a malonate derivative (VIII).

2-Amino-5-benzylthio-1,3,4-thiadiazole (III) can be prepared by a generally employed method for preparing known 1,3,4-thiadiazoles in accordance with the following reaction scheme:

| Compound No. | X | Y | m.p. (°C.) |
|---|---|---|---|
| 1 | H | H | 174~176 |
| 2 | CH₃ | " | 171~173 |
| 3 | C₂H₅ | " | 143~153 |
| 4 | i-C₃H₇ | " | 154~156 |
| 5 | i-C₃H₇ | " | 115~119 |
| 6 | phenyl | " | 166~167* |
| 7 | Cl | " | 219~221 |
| 8 | H | Cl | 182~187 |
| 9 | CH₃ | " | 211~213 |
| 10 | F | H | 203~205 |
| 11 | H | F | 186~190 |
| 12 | OCH₃ | H | 204~206 |
| 13 | OC₂H₅ | " | 198~201 |
| 14 | O-phenyl | " | 160~164 |
| 15 | H | C≡CH | 101~106 |
| 16 | " | C≡CCH₃ | 194~199 |
| 17 | " | CH₂Cl | 209~211 |
| 18 | " | CF₃ | 207~213 |
| 19 | " | C≡C-phenyl | 183~186 |
| 20 | " | CN | 214~217 |
| 21 | CH₃ | " | 203~216 |
| 22 | CN | H | 219~221 |
| 23 | NO₂ | Cl | 220~223 |
| 24 | " | OCH₃ | 216~218 |
| 25 | " | OC₂H₅ | 210~211 |
| 26 | Cl | CH₂Cl | 211~215 |

*decomposed

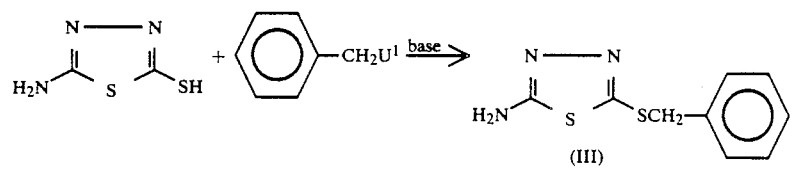

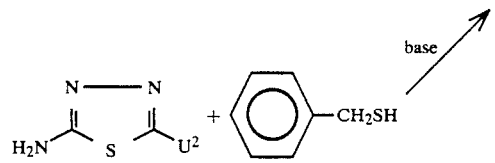

wherein $U^1$ and $U^2$ stand for a halogen atom.

Process A

The method using a β-ketoester derivative (IV)

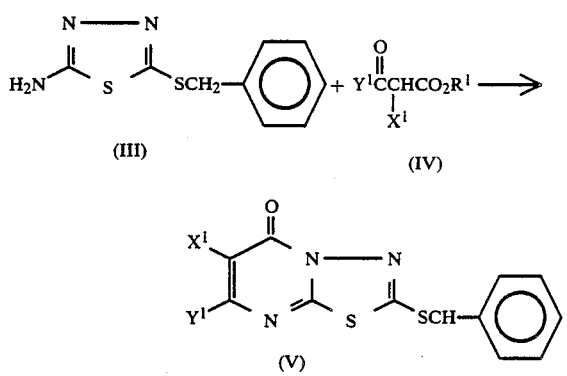

wherein $X^1$ is a hydrogen atom or a halogen atom, $Y^1$ is a haloalkyl group and $R^1$ is an alkyl group.

Compounds of general formula (V) can be prepared by reacting 2-amino-5-benzylthio-1,3,4-thiadiazole (III) with a compound of the formula (IV) in a high-boiling solvent, or in the presence of a condensation reagent such as polyphosphoric acid, boron trifluoride etherate, sulfuric acid, etc. in the presence or absence of a relatively high-boiling solvent such as xylene.

Compounds of the general formula (IV) are known or otherwise can be prepared by a conventional process. Some of them are commercially available.

Of the compounds of the general formula (V), of which $X^1$ is a halogen atom, can be prepared by halogenating a corresponding compound of which $X^1$ is a hydrogen atom. As halogenating agents, chlorine, sulfuryl chloride, bromine, iodine monochloride, etc. can be used for instance. If desired, a metal halide such as zinc chloride, ferric halide, etc. can be used as a catalyst. Also, zinc chloride, etc. can be used as a hydrogen halide acceptor.

Process B

The method using a β-formylester or 2-propenoate derivative.

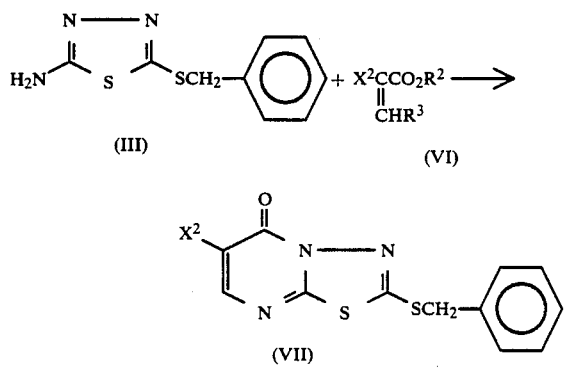

wherein $X^2$ is a hydrogen atom, a halogen atom, an alkyl group, an alkoxy group, a phenyl group or a phenoxy group, $R^2$ is an alkyl group and $R^3$ is a hydroxy group or an alkoxy group.

Compounds of the general formula (VII) can be prepared by reacting 2-amino-5-benzylthio-1,3,4-thiadiazole (III) with a compound of general formula (VI) in the same manner as in the above Process A.

Compounds of the general formula (VII) wherein $X^2$ is a halogen atom can be prepared by halogenating a compound of the general formula (VII) wherein $X^2$ is a hydrogen atom. Further, the halogen atom, preferably an iodine atom, as a substituent $X^2$, can be converted to a cyano group.

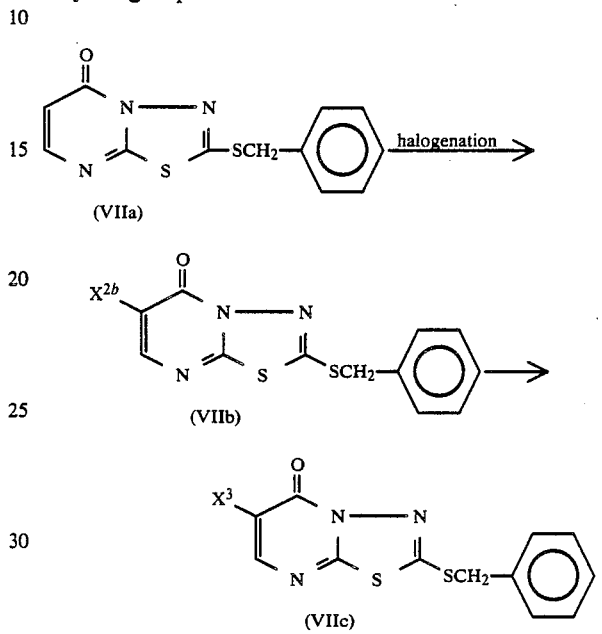

wherein $X^{2b}$ is a halogen atom and $X^3$ is a cyano group.

The halogenation can be carried out in the same manner as in the above-described Process A.

A halogen atom, preferably an iodine atom, as a substituent $X^{2b}$, can be converted to a cyano group. As a preferred cyanizing agent, sodium cyanide and cuprous cyanide are simultaneously used in the presence of dimethylformamide solvent.

Compounds of the general formula (VI) are known or otherwise can be prepared by a conventional process. Some of them are commercially available.

Process C

The method using a malonate derivative (VIII).

Compounds of the general formula (II), wherein Y is a halogen atom, an alkynyl group or a cyano group, can be prepared by the following process.

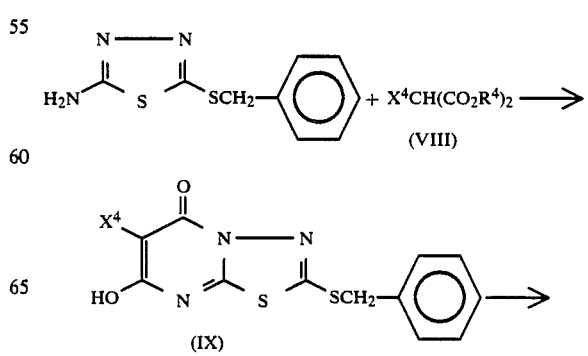

-continued

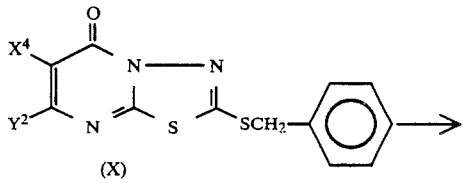

(X)

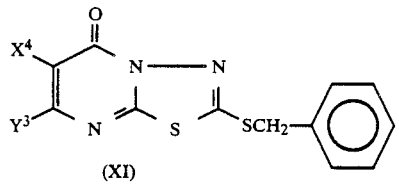

(XI)

wherein X⁴ is a hydrogen atom or an alkyl group, Y² is a halogen atom, Y³ is an alkynyl group or a cyano group and R⁴ is a phenyl group or a substituted phenyl group.

The reaction of 2-amino-5-benzylthio-1,3,4-thiadiazole (III) with a compound of the general formula (VIII) is carried out in a relatively high-boiling solvent such as chlorobenzene in accordance with the procedure described in Pharmazie 33, H 11–13 (1978). A hydroxy group of the compound of the general formula (IX) can be converted to a halogen atom by conventional method. If desired, compounds of the general formula (X) are subjected to halogen exchange. The halogen atom, preferably an iodine atom, can be converted to an alkynyl or a cyano group.

Examples of the usable halogenating agents are phosphorous oxychloride, phosphorous pentachloride, etc. If desired, a solvent such as toluene, a hydrogen halide acceptor such as N,N-dimethylaniline, etc. can be used. Halogen exchange can be performed by using hydroiodic acid, potassium fluoride, etc.

Compounds of the general formula (XI) wherein Y³ is a cyano group or an alkynyl group can be prepared by converting the halogen atom Y², preferably an iodine atom, of a compound of the general formula (X) to a cyano group in accordance with the cyanization procedure described in Process B, or to an alkynyl group by a method described below.

Compounds of the general formula (XI) wherein Y³ is an alkynyl group can be prepared by reacting a compound of the general formula (X) wherein Y² is a halogen atom, preferably, an iodine atom, with an alkyne compound such as an alkylacetylene, ethynyltrimethylsilane, etc. in the presence of a catalyst such as bis(triphenylphosphine)palladium (II) chloride, cuprous iodide, etc. and a hydrogen halide acceptor such as triethylamine. If necessary, the protecting group such as trimethylsilyl which is bonded to the alkynyl group is removed with a base such as potassium carbonate, tetraalkylammonium fluoride, etc.

Compounds of the general formula (IX) wherein X⁴ is a hydrogen atom can be nitrated, and thereafter the hydroxy group at the 7-position can be converted to a halogen atom, and further the halogen atom can be converted to an alkoxy group.

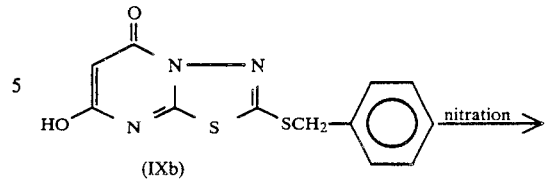

(IXb)

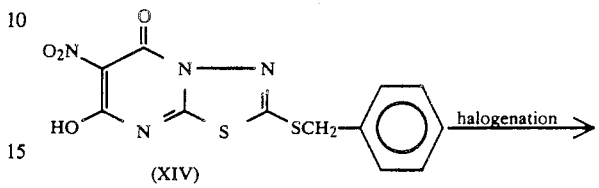

(XIV)

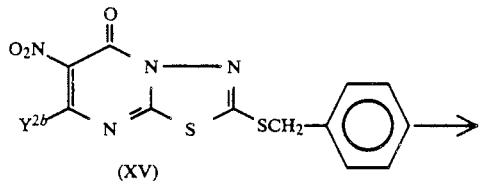

(XV)

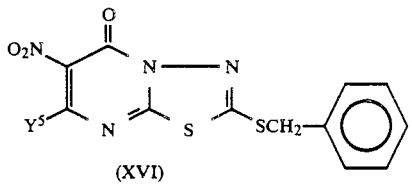

(XVI)

wherein $Y^{2b}$ is a halogen atom and $Y^5$ is an alkoxy group.

Compounds of the general formula (XIV) can be prepared by treating a compound of the general formula (IXb) with fuming nitric acid in the presence or absence of a solvent such as acetic acid if desired.

Compounds of the formula (XV) can be prepared in the same manner as the preparation of the compounds of the formula (X). Compounds of the formula (XVI) can be prepared by reacting a compound of the formula (XV) with an alcohol in the presence of a hydrogen halide acceptor such as pyridine, and a solvent if desired.

Compounds of general formula (XIII) are known or otherwise can be prepared by a conventional process.

The compounds of the present invention, that is, the 5H-1,3,4-thiadiazolo[3,2-a]pyrimidin-5-one derivatives of the general formula (I), of which the substituents are defined above, have excellent biological activities useful as agricultural-horticultural fungicides.

The compounds of the present invention can be used as agricultural-horticultural fungicides by themselves, but usually they are admixed with a carrier, a surfactant, a dispersant or an adjuvant by a conventional method, and prepared into dust preparations, wettable powder preparations, emulsifiable concentrate preparations, granular preparations or pellet preparations. Suitable carriers are solid carriers such as talc, bentonite, clay, kaolin, diatomaceous earth, white carbon, vermiculite, slaked lime, siliceous sand, ammonium sulfate, urea, etc.; liquid carriers such as isopropyl alcohol, xylene, cyclohexanone, etc. Examples of surfactant and dispersant are alcohol sulfate ester salts, alkylarylsulfonic acid salts, lignosulfonic acid salts, diarylmethanepolysulfonic acid salts, polyoxyethylenealkylaryl ether, polyoxyethylene sorbitane monoalkylate, etc. Examples of adjuvant are carboxymethyl cellulose, polyethylene glycol, gum arabic, etc. These preparations are applied per se, or are diluted to proper concentrations for application.

The concentration of the active ingredient in preparations is selected as occasion demands. However, in the case of dust or granular preparations, it is generally 0.5–20% by weight, and in the case of emulsion preparation and water-dispersed preparation, it is generally 5–80% by weight.

The amount of the agricultural-horticultural fungicide preparation of this invention varies in accordance with species of the used compound, kind of disease, tendency of affection, degree of damage, environmental conditions, type of preparation, etc. When a preparation is applied per se in the case of a dust or granular preparation, the concentration of the active ingredient is selected such that 10–500 g thereof is applied per 10 ares. In the case of emulsion or water-dispersed preparation, the concentration of the active ingredient is 10–2000 ppm.

The 5H-1,3,4-thiadiazolo[3,2-a]pyrimidin-5-one derivatives of the present invention are novel compounds and exhibit excellent control effect against pathogenic fungi of Alternaria sooty spot of Chinese mustard (*Brassica rapa* var. *pervidis*), leaf spot of apple, black spot of pear, etc. belonging to genus Alternaria, and also are able to control gray mold of cucumber, downy mildew of cucumber, rice blast, etc. This activity is exhibited both preventive and curative and is durable. Further, compounds are highly non-toxic to crop plants per se, and homoiothermic animals and aquatic animals.

DESCRIPTION OF SPECIFIC EMBODIMENTS

Now the invention will be illustrated in detail by way of working examples. Percentage referred to in examples is by weight.

PREPARATION EXAMPLE 1

Synthesis of 2-benzylthio-6-methyl-5H-1,3,4-thiadiazolo[3,2-a]pyrimidin-5-one

In a mixture of 40 ml of water and 45 ml of ethanol, 21.1 g of 2-amino-5-mercapto-1,3,4-thiadiazole and 6.9 g of sodium hydroxide were dissolved. To this solution, 19.6 g of benzyl chloride was added, and the mixture was stirred at 50° C. for 1 hour. After cooling, water was added to the reaction mixture, the formed precipitate was separated by filtration and washed with water and an ethanol/n-hexane (1:1) mixture respectively. The thus treated precipitate was dried under reduced pressure, and thus 32.5 g of 2-amino-5-benzylthio-1,3,4-thiadiazole was obtained. m.p. 159°–161° C. Yield 94%.

Five point six (5.6) grams of the thus obtained 2-amino-5-benzylthio-1,3,4-thiadiazole and 3.6 g of ethyl 3-hydroxy-2-methyl-2-propenoate were mixed with 7.5 g of polyphosphoric acid, and the mixture was stirred at 130°–150° C. for 45 minutes. After cooling, water was added to the reaction mixture, and the mixture was extracted with chloroform. The organic layer was washed with an aqueous sodium hydrogen carbonate solution and water respectively, and dried over anhydrous sodium sulfate. The solvent was distilled off, and the residue was recrystallized from ethanol. Thus 4.4 g of 2-benzylthio-6-methyl-5H-1,3,4-thiadiazolo[3,2-a]pyrimidin-5-one was obtained. m.p. 130°–132° C. Yield 61%.

PREPARATION EXAMPLE 2

Synthesis of 2-benzylthio-7-chloro-6-methyl-5H-1,3,4-thiadiazolo[3,2-a]pyrimidin-5-one A mixture of 19.3 g of 2-amino-5-benzylthio-1,3,4-thiadiazole, 41.3 g of bis(2,4,6-trichlorophenyl) 2-methylmalonate and 60 ml of chlorobenzene was stirred at 135°–140° C. for 1 hour. After cooling, n-hexane was added to the reaction mixture and the formed precipitate was separated by filtration. The separated precipitate was washed with n-hexane and thus 23.9 g of 2-benzylthio-7-hydroxy-6-methyl-5H-1,3,4-thiadiazolo[3,2-a]pyrimidin-5-one was obtained. m.p. 247°–250° C. Yield 91%.

A mixture of 18.3 g of the thus obtained 2-benzylthio-7-hydroxy-6-methyl-5H-1,3,4-thiadiazolo[3,2-a]pyrimidin-5-one, 13.1 g of phosphorus pentachloride and 36.8 g phosphorus oxychloride was stirred at 85°–95° C. for 1.5 hours. Thereafter, the reaction mixture was concentrated under reduced pressure, and the residue was dissolved in toluene. The organic layer was washed with an aqueous potassium carbonate solution and water respectively, and dried over anhydrous sodium sulfate. The solvent was distilled off and the residue was purified by silica gel column chromatography using an ethyl acetate/toluene (3:7) mixture as an eluent. Then the solvent was distilled off, and thus 14.0 g of 2-benzylthio-7chloro-6-methyl-5H-1,3,4-thiadiazolo[3,2-a]pyrimidin-5-one was obtained m.p. 102°–104° C. Yield 72%.

PREPARATION EXAMPLE 3

Synthesis of Compound 2

In 75 ml of ethanol, 2.8 g of 2-benzylthio-6-methyl-5H-1,3,4-thiadiazolo[3,2-a]pyrimidin-5-one prepared in Preparation Example 1 was added and dissolved by warming the mixture to 60° C. To this solution, an aqueous suspension of 35.7 g OXONE ® of in 150 ml of water was added, and the mixture was stirred at 60° C. for 2 hours. After cooling, water was added to dissolve inorganic materials, and the deposited crystals were collected by filtration. The crystals were recrystallized from ethanol, and thus 1.6 g of 2-benzylsulfonyl-6-methyl-5H-1,3,4-thiadiazolo[3,2-a]pyrimidin-5-one was obtained. m.p. 171°–173° C. Yield 52%.

PREPARATION EXAMPLE 4

Synthesis of Compound 9

Four point nine (4.9) grams of 2-benzylthio-7-chloro-6-methyl-5H-1,3,4-thiadiazolo[3,2-a]pyrimidin-5-one was dissolved in methanol. To this solution, an aqueous suspension of 69.2 g of OXONE ® in 240 ml of water was added, and the mixture was stirred at 60° C. for 1 hour and 45 minutes. After cooling, the reaction mixture was extracted with chloroform, the organic layer was washed with an aqueous sodium thiosulfate solution and water respectively and dried over anhydrous sodium sulfate. The solvent was distilled off, and the residue was recrystallized from a toluene/ethanol (1:1) mixture. Thus 3.3 g of 2-benzylsulfonyl-7-chloro-6-methyl-5H-1,3,4-thiadiazolo[3,2-a]pyrimidin-5-one was obtained. m.p. 211°–213° C. Yield 62%.

PREPARATION EXAMPLE 5

Synthesis of 2-benzylsulfonyl-6-methoxy-5H-1,3,4-thiadiazolo[3,2-a]pyrimidin-5-one (Compound 12)

In 155 ml of methanol, 5.1 g of 2-benzylthio-6-methoxy-5H-1,3,4-thiadiazolo[3,2-a]pyrimidin-5-one was dissolved. A suspension of 46.2 g of OXONE ® in 160 ml of water was added to the methanol solution, and the mixture was stirred at 60°-65° C. for 50 minutes. After cooling, the mixture was extracted with chloroform, and the organic layer was washed with an aqueous sodium thiosulfate solution, an aqueous sodium hydrogen carbonate solution and water. After the organic phase was dried over anhydrous sodium sulfate, the solvent was distilled off and the residue was recrystallized from a toluene/ethanol mixture, and thus 2.8 g of 2-benzylsulfonyl-6-methoxy-5H-1,3,4-thiadiazolo[3,2-a]pyrimidin-5-one was obtained. m.p. 204°-206° C. Yield 50%.

PREPARATION EXAMPLE 6

Synthesis of 2-benzylsulfonyl-7-ethynyl-5H-1,3,4-thiadiazolo[3,2-a]pyrimidin-5-one (Compound 15)

In 100 ml of acetic acid, 2.3 g of 2-benzylthio-7-ethynyl-5H-1,3,4-thiadiazolo[3,2-a]pyrimidin-5-one was dissolved. To this solution, 0.12 g of sodium tungstate dihydrate was added and the solution was warmed to 50° C. In 50 ml of acetic acid, 12.0 g of 30% hydrogen peroxide was dissolved and this solution was added dropwise into the acetic acid solution, and the resulting solution was warmed to 50°-60° C. and was stirred for one and half hours at that temperature. After cooling, the solution was diluted with water and extracted with chloroform. The organic layer was washed with an aqueous sodium thiosulfate solution and water, and dried over anhydrous sodium sulfate. The solvent was distilled off and the residue was washed with ethanol and thus 1.1 g of 2-benzylsulfonyl-7-ethynyl-5H-1,3,4-thiadiazolo[3,2-a]pyrimidin-5-one was obtained. m.p. 101°-106° C. Yield 43%.

PREPARATION EXAMPLE 7

Synthesis of 2-benzylthio-6-methoxy-5H-1,3,4-thiadiazolo[3,2-a]pyrimidin-5-one (intermediate)

In a mixture of 190 ml of water and 150 ml of ethanol, 70.3 g of 2-amino-5-mercapto-1,3,4-thiadiazole and 23.0 g of sodium hydroxide were dissolved. To this solution, 65.2 g of benzyl chloride was added and the resulting solution was warmed to 50° C. and stirred for 1 hour at this temperature. After cooling, water was added to the solution, and the formed precipitate was separated by filtration. The residue was washed with water and an ethanol/hexane mixture, and dried under reduced pressure. Thus 108.1 g of 2-amino-5-benzylthio-1,3,4-thiadiazole was obtained. m.p. 159°-161° C. Yield 94%.

Four (4) grams of the thus obtained 2-amino-5-benzylthio-1,3,4-thiadiazole, 3.2 g of propyl 3-hydroxy-2-methoxy-propenoate and 11 g of polyphosphoric acid were heated to 135° C. and stirred for 20 minutes. After cooling, chloroform and water were added thereto, extraction was carried out. The organic layer was washed with an aqueous sodium hydrogen carbonate solution and water, and dried over anhydrous sodium sulfate. The solvent was distilled off and the residue was washed with an ethanol/hexane mixture and 5.1 g of 2-benzylthio-6-methoxy-5H-1,3,4-thiadiazolo[3,2-a]pyrimidin-5-one was obtained. Yield 93%. The compound was recrystallized from ethanol. m.p. 145°-147° C.

PREPARATION EXAMPLE 8

Synthesis of 2-benzylthio-7-ethynyl-5H-1,3,4-thiadiazolo[3,2-a]pyrimidin-5-one (intermediate)

A mixture of 44.7 g of 2-amino-5-benzylthio-1,3,4-thiadiazole, 98.1 g of bis(2,4,6-trichlorophenyl) malonate and 140 ml of chlorobenzene was heated to 130°-140° C. and stirred for 20 minutes. After cooling, hexane was added to the mixture, and the formed precipitate was separated by filtration. The solid was washed with hexane and thus 57.1 g of 2-benzylthio-7-hydroxy-5H-1,3,4-thiadiazolo[3,2-a]pyrimidin-5-one was obtained. Yield 98%.

A mixture of 31.7 g of the thus obtained 2-benzylthio-7-hydroxy-5H-1,3,4-thiadiazolo[3,2-a]-pyrimidin-5-one, 24.0 g of phosphorus pentachloride and 117 g of phosphorus oxychloride was heated to 70°-80° C. and stirred for 25 minutes. After cooling, the reaction mixture was concentrated under reduced pressure and chloroform and water were added to the residue. The organic layer was washed with an aqueous sodium hydrogen carbonate solution and water, and dried over anhydrous sodium sulfate. The solvent was distilled off and the residue was separated by silica gel column chromatography using an ethyl acetate/hexane mixture as an eluent, and thus 8.5 g of 2-benzylthio-7-chloro-5H-1,3,4-thiadiazolo[3,2-a]pyrimidin-5-one was obtained. m.p. 138°-140° C. Yield 25%.

A mixture of 12.2 g of the thus obtained 2-benzylthio-7-chloro-5H-1,3,4-thiadiazolo[3,2-a]pyrimidin-5-one and 124 g of 57% hydroiodic acid was heated to 100°-105° C. and stirred for 4 hours. After cooling, the mixture was filtered and the solid was washed with water and dissolved in chloroform. The organic layer was washed with a sodium hydrogen carbonate aqueous solution, a sodium thiosulfate aqueous solution and water, and dried over anhydrous sodium sulfate. The solvent was distilled off and thus 13.9 g of 55% pure 2-benzylthio-7-iodo-5H-1,3,4-thiadiazolo[3,2-a]pyrimidin-5-one was obtained. Yield 48%.

In a mixture of 30 ml of triethylamine and 60 ml of tetrahydrofurane, 7.0 g of the thus obtained 55% pure 2-benzylthio-7-iodo-5H-1,3,4-thiadiazolo[3,2-a]pyrimidin-5-one was dissolved, and 0.68 g of bis(triphenylphosphine)palladium (II) chloride and 0.18 g of cuprous iodide were added to the solution. A solution of 3.8 g of ethynyltrimethylsilane in 20 ml of triethylamine was added dropwise to the above solution, the resulting solution was heated to 68°-70° C. and stirred for 4 hours. After cooling, the reaction mixture was filtered, and the filtrate was concentrated under reduced pressure. The residue was separated by silica gel column chromatography using an ethyl acetate/hexane mixture as an eluent, and thus 4.2 g of 2-benzylthio-7-trimethylsilylethynyl-5H-1,3,4-thiadiazolo[3,2-a]pyrimidin-5-one was obtained.

In 50 ml of tetrahydrofurane, 4.1 g of the thus obtained 2-benzylthio-7-trimethylsilylethynyl-5H-1,3,4-thiadiazolo[3,2-a]pyrimidin-5-one was dissolved and the solution was cooled to −65° C. with an acetone-dry ice bath. A solution of 0.16 g tetrabutylammonium fluoride in 50 ml tetrahydrofurane was added dropwise to the cooled solution, and the resulting solution was stirred at −60°−−65° C. for 10 minutes. After returning to room temperature, the reaction mixture was filtered, ether and water were added to the filtrate, and extraction was carried out. The organic layer was washed with water and dried over anhydrous sodium sulfate. The solvent was distilled off and the residue was separated by silica gel column chromatography using an ethyl acetate/hexane mixture as an eluent, and thus 2.3 g of 2-benzylthio-7-ethynyl-5H-1,3,4-thidadiazolo[3,2-a]pyrimidin-5-one was obtained. m.p. 112°–120° C. Yield 65%.

PREPARATION EXAMPLE 9

Synthesis of 2-benzylsulfonyl-7-cyano-5H-1,3,4-thiadiazolo[3,2-a]pyrimidin-5-one Three (3) grams of 2-benzylthio-7-cyano-5H-1,3,4-thiadiazolo[3,2-a]pyrimidin-5-one was dissolved in 60 ml of acetic acid. To this solution, 0.12 g of sodium tungstate dihydrate was added, and the solution was warmed to 45° C. To this acetic acid solution, a solution of 5.6 g of a 30% hydrogen peroxide solution in 30 ml of acetic acid was added dropwise. Thereafter, the solution was stirred at 45°–50° C. for 3 hours. After the reaction was finished, the reaction mixture was cooled to room temperature, diluted with water, and extracted with chloroform. The organic layer was washed with an aqueous sodium thiosulfate solution and water respectively, and dried over anhydrous sodium sulfate. The solvent was distilled off, the residue was recrystallized from ethanol, and 1.1 g of 2-benzylsulfonyl-7-cyano-5H-1,3,4-thiadiazolo[3,2-a]pyrimidin-5-one was obtained. m.p. 214°–217° C. Yield 33%.

PREPARATION EXAMPLE 10

Synthesis of 2-benzylsulfonyl-6-cyano-5H-1,3,4-thiadiazolo[3,2-a]pyrimidin-5-one In 10 ml of acetic acid, 0.3 g of 2-benzylthio-6-cyano-5H-1,3,4-thiadiazolo[3,2-a]pyrimidin-5-one was dissolved, and 17 mg of sodium tungstate dihydrate was added thereto. To this solution, 2.3 g of a 30% hydrogen peroxide solution was added dropwise slowly lest the temperature of the reaction mixture should exceed 50° C. After the addition of the hydrogen peroxide was finished, the reaction mixture was stirred at 50° C. for 3 hours. After the reaction was finished, the reaction mixture was cooled and diluted with water. The deposited crystals were collected by filtration and washed with water. The crude crystals were recrystallized from ethanol and thus 0.17 g of 2-benzylsulfonyl-6-cyano-5H-1,3,4-thiadiazolo[3,2-a]pyrimidin-5-one was obtained. m.p. 219°–221° C. Yield 51%.

PREPARATION EXAMPLE 11

Synthesis of 2-benzylsulfonyl-7-methoxy-6-nitro-5H-1,3,4-thiadiazolo[3,2-a]pyrimidin-5-one In 20 ml of acetic acid, 2.1 g of 2-benzylthio-7-methoxy-6-nitro-[3,2-a]pyrimidin-5-one was dissolved, and 0.1 g of sodium tungstate dihydrate was added thereto. To this solution, 2 g of a 30% hydrogen peroxide solution was added dropwise slowly lest the temperature of the reaction mixture should exceed 50° C. After the addition of the hydrogen peroxide was finished, the reaction mixture was stirred at 50° C. for 1 hour. After the reaction was finished, the reaction mixture was cooled and diluted with water. The deposited crystals were collected by filtration and washed with water. The crude crystals were recrystallized from ethanol and thus 1.8 g of 2-benzylsulfonyl-7-methoxy-6-nitro-5H-1,3,4-thiadiazolo[3,2-a]pyrimidin-5-one was obtained. m.p. 216°–218° C. Yield 80%.

PREPARATION EXAMPLE 12

Synthesis of 2-benzylthio-7-cyano-7-5H-1,3,4-thiadiazolo[3,2-a]pyrimidin-5-one

In 120 ml of dimethylformamide, 9 g of 90% pure 2-benzylthio-7-iodo-5H-1,3,4-thiadiazolo[3,2-a]pyrimidin-5-one was dissolved, and 3.05 g of cuprous cyanide and 1.57 g of sodium cyanide were added thereto. The reaction mixture was heated to 100° C. and stirred at that temperature for 1 hour. After the reaction was finished, the reaction mixture was cooled, diluted with water and extracted with chloroform. The organic layer was washed with water, and the chloroform was distilled off. Water was added to the residue and the mixture was extracted with toluene. The organic layer was washed with water and dried over anhydrous sodium sulfate. Florisil ® was added to the dried organic layer, and the organic layer was shaken well. After the Florisil ® was separated, the solvent was distilled off, and thus 3.0 g of 2-benzylthio-7-cyano-5H-1,3,4-thiadiazolo[3,2-a]pyrimidin-5-one was obtained. Yield 50%. (Florisil ® (a registered trademark of Floridin Company) is a highly selective magnesium silicate absorbent.)

PREPARATION EXAMPLE 13

Synthesis of 2-benzylthio-6-cyano-5H-1,3,4-thiadiazolo[3,2-a]pyrimidin-5-one

Fifteen point five (15.5) grams of 2-amino-5-benzylthio-1,3,4-thiadiazole, 10 g of ethyl 3-ethoxypropenoate, 15 g of polyphosphoric acid and 15 ml of xylene were mixed and vigorously stirred for 30 minutes. After the reaction was finished, the reaction mixture was cooled. Water was added to the reaction mixture and the mixture was extracted with toluene. The organic layer was washed with an aqueous sodium hydrogen carbonate solution and water respectively and dried over anhydrous sodium sulfate. The solvent was distilled off, the residue was recrystallized from an ethanol/hexane mixture, and thus 10.3 g of 2-benzylthio-5H-1,3,4-thiadiazolo[3,2-a]pyrimidin-5-one was obtained. Yield 54%.

Five (5) grams of the thus obtained 2-benzylthio-5H-1,3,4-thiadiazolo[3,2-a]pyrimidin-5-one, 5 g of zinc chloride were added to 50 ml of acetic acid. Six (6) grams of iodine monochloride was added to the mixture, and the mixture was stirred at 70°–80° C. for 1 hour. After the reaction was finished, the reaction mixture was cooled and a sodium chloride solution was added. The deposited crystals were collected by filtration, washed with water and isopropyl ether and thus 1.3 g of 2-benzylthio-6-iodo-5H-1,3,4-thiadiazolo[3,2-a]pyrimidin-5-one was obtained. Yield 18%.

One point three (1.3) grams of the thus obtained 2-benzylthio-6-iodo-5H-1,3,4-thiadiazolo[3,2-a]pyrimidin-5-one was dissolved in 15 ml of dimethylformamide. To this solution, 0.6 g of cuprous cyanide and 0.3 g of sodium cyanide were added, and the mixture was stirred at 130° C. for 3 hours. After the reaction was finished, the reaction mixture was cooled, water and toluene were added to the mixture and the mixture was stirred well. The mixture was filtered to remove insoluble materials. The organic layer of the filtrate was washed with water, and dried over anhydrous magnesium sulfate. The solvent was distilled off under reduced pressure. The obtained crude crystals were recrystallized from ethanol, and thus 0.3 g of 2-benzylthio-6-5H-1,3,4-thiadiazolo[3,2-a]pyrimidin-5-one was obtained. Yield 31%.

PREPARATION EXAMPLE 14

Synthesis of 2-benzylthio-7-methoxy-6-nitro-5H-1,3,4-thiadiazolo[3,2-a]pyrimidin-5-one Twenty-four (24) grams of 2-benzylthio-7-hydroxy-5H-1,3,4-thiadiazolo[3,2-a]pyrimidin-5-one was suspended in 250 ml of acetic acid and warmed to 40° C. To this suspension, 7.9 g of fuming nitric acid was added dropwise. After the addition of the nitric acid was finished, the reaction mixture was stirred at 40° C. for 5 hours. After the reaction was finished, the reaction mixture was cooled, and water was added thereto. The deposited crystals were collected by filtration, washed with water and dried under reduced pressure. Thus 24 g of 2-benzylthio-7-hydroxy-6-nitro-5H-1,3,4-thiadiazolo[3,2-a]pyrimidin-5-one was obtained. Yield 87%.

Twenty-four (24) grams of the thus obtained 2-benzylthio-7-hydroxy-6-nitro[3,2-a]pyrimidin-5-one, 40 ml of phosphorus oxychloride and 8.6 g of N,N-dimethylaniline were mixed and the mixture was stirred under refluxing for 30 minutes. After the reaction was finished, the reaction mixture was concentrated under reduced pressure. The residue was dissolved in toluene. The toluene solution was meticulously washed with water twice and then with an aqueous sodium hydroxide solution. Further the solution was washed with water until the washings became neutral. Then the toluene solution was dried over anhydrous magnesium sulfate, and treated with Florisil ®. The solvent was distilled off under reduced pressure and the residue was washed with isopropyl ether and thus 19.5 g of 2-benzylthio-7-chloro-6-nitro-5H-1,3,4-thiadiazolo[3,2-a]pyrimidin-5-one was obtained. Yield 77%.

Three (3) grams of the thus obtained 2-benzylthio-7-chloro-6-nitro-5H-1,3,4-thiadiazolo[3,2-a]pyrimidin-5-one was dissolved in 50 ml of methanol, and 0.8 g of pyridine was added. The solution was stirred under refluxing for 30 minutes. After the reaction was finished, the reaction mixture was cooled and poured into water. The resulting mixture was extracted with toluene. The organic layer was washed with water and dried over anhydrous magnesium sulfate. The solvent was distilled off under reduced pressure and the residue was washed with isopropyl ether. Thus, 2.1 g of 2-benzylthio-7-methoxy-6-nitro-5H-1,3,4-thiadiazolo[3,2-a]pyrimidin-5-one was obtained. Yield 70%.

FORMULATION EXAMPLE 1

Dust preparation

Two percent (2%) Compound 1, 5% diatomaceous earth and 93% clay were homogeneously mixed and ground to give a dust preparation.

FORMULATION EXAMPLE 2

Wettable powder

Fifty percent (50%) Compound 2, 45% diatomaceous earth, 2% sodium dinaphthylmethanesulfonate and 3% sodium lignosulfonate were homogeneously mixed and ground to give a wettable powder preparation.

FORMULATION EXAMPLE 3

Emulsifiable concentrate

Thirty percent (30%) Compound 3, 20% cyclohexanone, 11% polyoxyethylenealkylaryl ether, 4% calcium alkylbenzenesulfonate and 35% methylnaphthalene were homogeneously mixed to give an emulsifiable preparation.

FORMULATION EXAMPLE 4

Granular preparation

Five percent (5%) Compound 4, 2% sodium salt of lauryl alcohol sulfate ester, 5% sodium lignosulfonate, 2%carboxymethyl cellulose and 86% clay were homogeneously mixed and ground. This mixture was kneaded with addition of 20% water, and made into 14–32 mesh granules by means of an extrusion granulating machine. The granules were dried.

Test 1

Protective Effect on Alternaria sooty spot of Chinese mustard (*Brassica rapa* var. *pervidis*)

Seeds of Chinese mustard were sown in 9 cm × 9 cm plastic pots, 12 seeds each in a pot, and grown for 7 days in a greenhouse to the cotyledonous stage. Onto the grown seedlings a water-dispersible preparation prepared in accordance with the above Formulation Example 2, which was diluted with water to 50 ppm, was sprayed at a rate of 10 ml per pot. After the sprayed preparation was air-dried, the plants were inoculated with a suspension of spores of the pathogenic fungus of Alternaria sooty spot disease (*Alternaria brassicicola*) by spraying and the pots were kept in a moist chamber at 30° C. After 3 days, number of lesions was counted and average numbers per leaf were recorded. The control value was calculated in accordance with the following definition.

Control Value (%) =

$$\left(1 - \frac{\text{Average no. of lesions in treated sections}}{\text{Average no. of lesions in non-treated sections}}\right) \times 100$$

TABLE 2-1 TABLE 2-2

| Compound Tested | Control Value |
| --- | --- |
| 1 | 85.4 |
| 2 | 90.1 |
| 3 | 93.5 |
| 4 | 92.5 |
| 6 | 90.6 |
| 7 | 93.2 |
| 8 | 75.0 |
| 9 | 89.3 |
| Captan | 50.8 |
| 10 | 93.2 |
| 11 | 88.3 |
| 12 | 86.9 |
| 13 | 71.4 |
| Captan | 52.4 |

Test 2

Control of apple Alternaria leaf spot

Young twigs with 6–7 leaves detached from an apple tree (variety: Indo) were put in a glass cylinder. A water-dispersible preparation prepared in accordance with the above Formulation Example 2 was diluted to 1500 ppm with water and sprayed thereonto. After air-dried, the plants were inoculated with a suspension of spores of the pathogenic fungus of Alternaria leaf spot (*Alternaria mali*) by spraying, and were kept in a moist chamber at 28° C. After 4 days, the damage index was worked out in accordance with the following standard and the control value was calculated.

Damage Index (%) =

$$\frac{(n_1 \times 1) + (n_2 \times 2) + (n_3 \times 3) + (n_4 \times 4) + (n_5 \times 5)}{5N} \times 100$$

$N$ is the total number of the examined leaves.
$n_0$ is the number of the unaffected leaves
$n_1$ is the number of the affected leaves on which area of lesions is less than 5%
$n_2$ is the number of the affected leaves on which area of lesions is less than 5–10%
$n_3$ is the number of the affected leaves on which area of lesions is less than 11–25%
$n_4$ is the number of the affected leaves on which area of lesions is less than 26–50%
$n_5$ is the number of the affected leaves on which area of lesions is more than 51%

Control Value (%) =

$$\left(1 - \frac{\text{Damage index in treated sections}}{\text{Damage index in untreated sections}}\right) \times 100$$

The results are shown in Table 3.

TABLE 3

| Compound Tested | Control Value |
| --- | --- |
| 2 | 90.0 |
| 4 | 87.3 |
| 6 | 70.0 |
| 8 | 77.7 |

Test 3

Prevention of cucumber gray mold

Seeds of cucumber (variety: Sagami-hanjiro) were sown in 9 cm × 9 cm square plastic pots, 12 seeds each in a pot, and grown in a greenhouse for 7 days. Onto the young seedlings, which have grown to the cotyledonous stage, a water-dispersible preparation prepared in accordance with the above Formulation Example 2, which was diluted to the active ingredient concentration of 500 ppm with water, was sprayed at a rate of 10 ml per pot. After the sprayed preparation was air-dried, the plants were inoculated with a homogenized hyphal suspension of liquid culture of cucumber gray mold fungus (Botrytis cinearea) by spraying, and the pots were kept in a moist chamber at 20°–23 C. After four days, conditions of the affection were checked with respect to all the pots.

0: No affection
1: Affected area is less than 25%
2: Affected area is less than 26–50%
3: Affected area is less than 51–75%
4: Affected area is more than 75%

The results are shown in Table 4.

TABLE 4

| Compound Tested | Index of Affection |
| --- | --- |
| 1 | 0 |
| 2 | 0 |
| 3 | 0 |
| 4 | 0 |
| 5 | 0 |
| 6 | 0 |
| 7 | 0 |
| 8 | 0 |
| 9 | 1 |
| 10 | 0 |
| 11 | 0 |
| 12 | 0 |
| 13 | 1 |
| 14 | 1 |
| 15 | 1 |
| 16 | 0 |
| 17 | 0 |
| Untreated | 4 |

Test 4

(Test on the preventive effects for cucumber downy mildew, *Pseudoperonospora cubensis*)

Cucumber seeds (cv. Sagamihanjiro) were sown at a rate of 12 seeds each in a plastic pot of 9 cm × 9 cm. The seeds were allowed to grow in a greenhouse for 7 days. A wettable powder containing a test compound and formulated in accordance with the Formulation Example 2 was diluted with water to a concentration of 500 ppm of the active ingredient, and the aqueous preparation obtained was then applied at a rate of 10 ml per pot to the cucumber seedlings at their cotyledonous stage. After dried in the air, the seedlings were inoculated with a spore suspension of cucumber downy mildew fungus, *Pseudoperonospora cubensis* and then placed in a moist chamber at 20°–22° C. On the 7th day after the inoculation disease severity was examined. The disease index and control value (%) were calculated by the following definitions.

Disease rating $n_0$: No. of healthy leaves
$n_1$: No. of leaves infected less than $\frac{1}{3}$
$n_2$: No. of leaves infected $\frac{1}{3}$ to $\frac{2}{3}$
$n_3$: No. of leaves infected more than $\frac{2}{3}$ Disease index =

$$\left(\frac{(n_0 \times 0) + (n_1 \times 1) + (n_2 \times 2) + (n_3 \times 3)}{3N}\right) \times 100$$

wherein N indicates total number of leaves examined.

Control Value (%) =

$$\left(1 - \frac{\text{Disease index in treated sections}}{\text{Disease index in untreated sections}}\right) \times 100$$

The results are indicated in Table 5.

TABLE 5

| Compound Tested | Control Value |
| --- | --- |
| 2 | 90.9 |
| 5 | 83.3 |
| 7 | 95.5 |
| 13 | 80.0 |
| 15 | 91.7 |
| 16 | 100.0 |
| 20 | 100.0 |

We claim:

1. A method of protecting plants against agricultural or horticultural fungi, comprising applying to a plant, a fungicidally effective amount of a 5H-1,3,4,-thiadiazolo[3,2-a]pyrimidin-5-one represented by the formula (I)

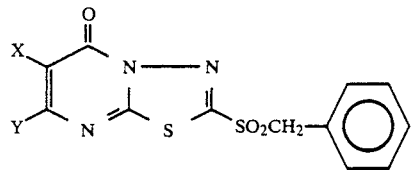

wherein X is a hydrogen atom, a halogen atom, an alkyl group or a phenyl group; and Y is a hydrogen atom or a halogen atom.

2. The method of claim 1, wherein X is a hydrogen atom, a halogen atom, a lower alkyl group or a phenyl group; and Y is a hydrogen atom or a halogen atom.

3. The method of claim 2, wherein X is a hydrogen atom, a halogen atom, a methyl group, an ethyl group or a phenyl group; and Y is a hydrogen atom or a halogen atom.

4. The method of claim 3, wherein X is a hydrogen atom and Y is a hydrogen atom or a halogen atom.

5. The method of claim 3, wherein X is a halogen atom, a methyl group, an ethyl group or a phenyl group and Y is a hydrogen atom.

6. The method of claim 1, wherein said pyrimidin-5-one is 2-benzylsulfonyl-6-methyl-5H-1,3,4-thiadiazolo-pyrimidin-5-one, 2-benzylsulfonyl-6-chloro-5H-1,3,4-thiadiazolo-pyrimidin-5-one, or 2-benzylsulfonyl-5H-1,3,4-thiadiazolo-pyrimidin-5-one.

* * * * *